United States Patent [19]

Onikata et al.

[11] Patent Number: 5,292,908
[45] Date of Patent: Mar. 8, 1994

[54] MODIFIED BENTONITE

[75] Inventors: Masanobu Onikata, Gunma; Mitsuji Kondo, Tochigi, both of Japan

[73] Assignee: Hojun Kogyo Co., Ltd., Annaka, Japan

[21] Appl. No.: 3,049

[22] Filed: Jan. 11, 1993

[30] Foreign Application Priority Data

Mar. 9, 1992 [JP] Japan .................. 4-85055

[51] Int. Cl.$^5$ .................. C07F 5/06
[52] U.S. Cl. .................. 556/173
[58] Field of Search .................. 556/173

[56] References Cited

U.S. PATENT DOCUMENTS

| | | |
|---|---|---|
| 2,531,427 | 11/1950 | Hauser .................. 260/448 |
| 4,287,086 | 9/1981 | Finlayson et al. .................. 556/173 X |
| 4,402,881 | 9/1983 | Alther .................. 556/173 |
| 4,407,728 | 10/1983 | Ball et al. .................. 556/173 X |
| 4,469,639 | 9/1984 | Thompson et al. .................. 556/173 X |
| 4,474,705 | 1/1984 | Clay et al. .................. 556/173 |
| 4,474,706 | 10/1984 | Clay et al. .................. 556/173 |
| 4,528,038 | 7/1985 | Williams .................. 556/173 X |
| 4,874,728 | 10/1989 | Elliott et al. .................. 501/148 |
| 5,110,501 | 5/1992 | Knudson et al. .................. 556/173 X |

FOREIGN PATENT DOCUMENTS 33-3018   4/1958   Japan .
57-111371 7/1982   Japan .

*Primary Examiner*—Paul F. Shaver
*Attorney, Agent, or Firm*—Kenyon & Kenyon

[57] ABSTRACT

Modified bentonite is disclosed, comprising modified bentonite which can be dispersed in water to perform a function of adjusting rheology of an aqueous liquid.

3 Claims, No Drawings

MODIFIED BENTONITE

FIELD OF THE INVENTION

This invention relates to surface-modified bentonite which is dispersible in water or organic liquids to exhibit an excellent function of adjusting rheology.

BACKGROUND OF THE INVENTION

Bentonite deposit has a complicated composition mainly formed of smectites and containing free silica minerals, such as quartz, $\alpha$-cristobalite, and opal; silicate minerals, such as feldspar, mica, and zeolite; carbonates or sulfates of alkaline earth metals, such as calcite, dolomite, and gypsum; and, in addition, iron compounds and humus. Since bentonite ore mined from bentonite deposit usually has a water content of 15 to 35%, it is primarily broken and dried in the sun or hot air to obtain bentonite ore having a water content of 5 to 10%. The dried bentonite ore is pulverized by means of an attrition grinding machine, such as a centrifugal roller mill, or an impact mill, such as a hammer mill. The resulting bentonite powder is widely used in various industrial fields, for example, as a binder for foundry sand, a main ingredient for a drilling fluid used in oil well drilling, geothermal well drilling, or hot spring boring, or a main agent of a stabilizing liquid used in continuous diaphragm wall construction or earth drilling in engineering works. As stated above, bentonite for these uses basically has a composition based on the natural bentonite deposit, containing much non-clay substances.

On the other hand, liquid fine chemicals widely used in various industrial fields, such as coatings, printing inks, and cosmetics, contain various natural or chemical substances for rheological adjustment. Purified bentonite powder, which is obtained by dispersing bentonite in water, removing unfavorable non-clay substances by spontaneous sedimentation or centrifugal separation, and drying the resulting purified bentonite sol by evaporation, is used as a rheological adjuster for aqueous coatings, aqueous emulsions, or the like aqueous colloidal dispersion products.

Because the bentonite powder which is merely purified can not be dispersed in organic-solvents, it is not suitable as a rheological adjuster for liquid products containing an organic solvent, such as alkyd resin coatings or other synthetic resin coatings, printing inks, and sealants. Hence, the purified bentonite is rendered organophilic by combining with a quaternary ammonium cation (see U.S. Pat. No. 2,531,427), a composite of a quaternary ammonium cation and a nonionic organic compound (see Japanese Patent 244306 corresponding to JP-B-3018 (The term "JP-B" as used herein means an examined Japanese patent publication), or a combination of a quaternary ammonium cation and an organic anion (see JP-A-57-111371), (the term "JP-A" as used herein means an "unexamined published Japanese patent applications") to be used as a rheological adjuster which can be dispersed in organic liquids.

However, the above-mentioned purified bentonite or organophilic modified bentonite has disadvantages as described below.

Purified bentonite exhibits unique rheological characteristics which differ from that of organic (high) polymers, e.g., carboxymethyl cellulose, poly(sodium acrylate), and polyacrylamide. However, because its function in increasing viscosity is generally insufficient, it must be added in a considerable proportion to obtain a sufficient effect in increasing viscosity, which leads to generation of various undesired side effects, such as impairment of the color tone of products. Accordingly, the amount of the purified bentonite incorporated is limited.

Organophilic modified bentonite has insufficient dispersibility in a solvent system comprising hydrocarbons only, and it is necessary to add to the dispersion system an adequate amount of a highly polar organic compound having a low molecular weight, such as methanol, ethanol, or acetone, to obtain organophilic modified bentonite which is sufficiently dispersed. However, such usage is not only complicated but involves a problem that an unfavorable polar compound should be introduced into the system.

SUMMARY OF THE INVENTION

An object of the present invention is to provide modified bentonite which can be dispersed in an aqueous system to provide an excellent effect in increasing viscosity which has not been achieved with conventional purified bentonite products.

Another object of the present invention is to provide organophilic modified bentonite which can easily be dispersed in a hydrocarbon solvent system to provide an excellent effect in increasing viscosity without use of a highly polar organic compound.

The inventors have found that the above objects of the present invention are accomplished by purified bentonite treated with an alkyltrialkoxysilane.

The present invention relates to modified bentonite which can be dispersed in water to perform a function of adjusting rheology of an aqueous liquid, which is obtained by adding at least one alkyltrialkoxysilane represented by formula (I):

$$R^1Si(OR^2)_3 \qquad (I)$$

wherein $R^1$ represents a saturated alkyl group having from 1 to 22 carbon atoms; and $R^2$ represents a methyl group, an ethyl group, a propyl group or a butyl group, to bentonite in such an amount that the resulting product can retain an excellent water-dispersibility, and then stirring and grinding the mixture in a water-free atmosphere to add an alkylsilyl group to a part of the surface of bentonite particles.

The present invention also relates to modified bentonite which can be easily dispersed in an organic liquid to perform a function of adjusting rheology of an organic liquid, which is obtained by adding to bentonite (1) from 1 to 1.5 equivalent of a quaternary ammonium cation represented by formula (II):

$$R^3 \cdot R^4 N^+ R^5_2 \qquad (II)$$

wherein $R^3$ represents a long-chain alkyl group having from 12 to 22 carbon atoms; $R^4$ represents a methyl group, a benzyl group or a long-chain alkyl group having from 12 to 22 carbon atoms; and $R^5$ represents a methyl group, based on the cation exchange capacity of said bentonite and (2) from 0.5 to 15 parts by weight of at least one alkyltrialkoxysilane represented by formula (I):

$$R^1Si(OR^2)_3 \qquad (I)$$

wherein $R^1$ and $R^2$ each has the same meaning as defined above, per 100 parts by weight of said bentonite to render said bentonite hydrophobic.

DETAILED DESCRIPTION OF THE INVENTION

Bentonite which can be used as a raw material in the present invention is substantially water-free purified bentonite which is obtained by removing non-clay substances from a crude bentonite suspension using spontaneous sedimentation or centrifugal separation to recover a purified bentonite sol, evaporating the resulting purified bentonite sol, and finally drying at a temperature of from 150 to 200° C.

The modified bentonite which can provide an excellent effect in increasing viscosity in an aqueous dispersion system according to the present-invention can be prepared by adding to purified bentonite in a water-free atmosphere an alkyltrialkoxysilane of the above formula in such an amount that does not cause the resulting product to exhibit water repellency, and, after stirring, grinding the mixture to thereby add an alkylsilyl group to a part of the surface of bentonite particles.

Specific examples of the alkyltrialkoxysilane represented by formula (I) which can be used in the present invention include methyltrimethoxysilane, methyltriethoxysilane, propyltrimethoxysilane, butyltrimethoxysilane, hexyltrimethoxysilane, octyltriethoxysilane, dodecyltriethoxysilane, and octadecyltriethoxysilane. Among these, hexyltrimethoxysilane, octyltriethoxysilane, dodecyltriethoxysilane, and octadecyltriethoxysilane are preferred.

The amount of the alkyltrialkoxysilane to be added to purified bentonite is experimentally decided from the degree of non-water repellency, wetting with water, and waterdispersibility of the finally obtained modified bentonite. In most cases, while not limiting, such an amount ranges generally from 0.5 to 15 parts by weight, preferably from 1 to 10 parts by weight, and most preferably from 1 to 7 parts by weight, per 100 parts by weight of bentonite.

By the treatment with the alkyltrialkoxysilane, an alkylsilyl group is added to hydrophilic hydroxyl groups present on the surface of bentonite particles, such as a silanol group, to render the part of the bentonite surface hydrophobic. The thus modified bentonite particles, when dispersed in an aqueous system, form a plastic structure due to association of the hydrophobic groups thereof and, as a result, considerably increase the apparent viscosity of the aqueous system and endow the aqueous system with favorable thixotropic properties.

The organophilic modified bentonite containing an alkylsilyl group for organic liquids, particularly hydrocarbon solvent systems, according to the present invention is preferably prepared by dissolving an alkyltrialkoxysilane in a quaternary ammonium cation solution, immediately adding the solution to a purified bentonite sol to conduct a reaction, followed by dehydration, drying, and pulverizing. The organophilic modified bentonite may also be prepared by re-dispersing in water the abovementioned alkyltrialkoxysilane-treated bentonite produced in a water-free atmosphere and then adding thereto a quaternary ammonium cation. However, the latter method is not practical because it requires re-dehydration and re-pulverizing, thus increasing cost.

Specific examples of the alkyltrialkoxysilane which can be used in the preparation of the organophilic modified bentonite are the same as those enumerated above.

The amount of the alkyltrialkoxysilane added ranges from 0.5 to 15 parts by weight per 100 parts by weight of bentonite.

The quaternary ammonium cation represented by formula (II) shown above which can be used in the present invention can be added in the form of a quaternary ammonium chloride. The amount of the quaternary ammonium cation added (i.e., the amount of the quaternary ammonium cation added) ranges from 1 to 1.5 equivalent and preferably from 1 to 1.25 quivalent, based on the cation exchange capacity of the starting bentonite.

By the above-mentioned treatment with the quaternary ammonium cation and alkyltrialkoxysilane, the alkyltrialkoxysilane is solubilized by a quaternary ammonium salt having surface activity and, at the same time, undergoes partial hydrolysis to form an alkylsilyl polymer, which is added to the hydrophilic sites on the surface of bentonite particles together with the quaternary ammonium cation to thereby accomplish a treatment for rendering the bentonite surface hydrophobic to such a degree that a quaternary ammonium cation alone cannot achieve. The resulting modified bentonite particles are easily dispersed in a hydrocarbon organic liquid to form a plastic structure due to association of the hydrophobic particles, with which a high apparent viscosity and favorable thixotropic properties can be imparted to the organic liquid system.

Bentonite which can be used in the present invention belongs to phyllosilicate minerals having a dioctahedral structure and/or a trioctahedral structure and having substantially a cation exchange capacity, which are selected from the group consisting of montmorillonite, beidellite, nontronite, hectorite and saponite, and further the bentonite may be artificial phyllosilicates.

The present invention is now illustrated in greater detail with reference to Examples, but it should be understood that the present invention is not deemed to be limited thereto. All the percents and parts are by weight unless otherwise indicated.

EXAMPLE 1

One kilogram of bentonite produced in Wyoming, U.S.A. was poured into 50 kg of deionized water and allowed to stand overnight to be swollen. Then the mixture was dispersed in a disper for 1 hour, and the resulting bentonite suspension was centrifuged at 4,000 rpm for 10 minutes to recover 43.5 kg of the supernatant purified bentonite sol (solids content: 1.03%). The purified bentonite sol was dried in a hot air circulator at 100° C. to obtain flaky purified bentonite having a water content of 6%. The flaky purified bentonite was ground in Bantam Mill (manufactured by Hosokawa K.K.) to a size of 250 mesh and dried at 200° C. for 2 hours to obtain 425 g of water-free bentonite.

Fifty grams of the water-free bentonite were put in a 1000 ml-volume ceramic pot mill, and 1 g of alkyltrialkoxysilane shown in Table 1 below each was added thereto. After sealing, the mill was rotated for 30 minutes to prepare alkyltrialkoxysilane-modified bentonite (Samples 1 to 8).

Each of Samples 1 to 8 and the non-treated purified bentonite as prepared above was dispersed with water in a Hamilton Beach Mixer (manufactured by Hamilton Beach Inc.,), and the rheological characteristics of the aqueous dispersion solution were measured with a Fann Viscometer (Model 35 SA" manufactured by Fann Instrument Corp.) at 23° C. Thixotropy was expressed in terms of a ratio of apparent viscosity at 300 rpm ($V_{300}$) to apparent viscosity at 600 rpm ($V_{600}$) (i.e., $V_{300}/V_{600}$). The results obtained are shown in Table 1.

ples 201 and 202). The cation exchange capacity of the purified bentonite was 72 milliequivalents per 100 g. The quaternary ammonium cation was added in an amount of 83 milliequivalents per 100 g of bentonite (i.e., water-free bentonite).

Samples 201 and 202 were compared with various commercially available organophilic modified benton-

TABLE 1

| Sample No. | Silane Treating Agent | Concentration (part*) | Apparent Viscosity $V_{300}$ (cps) | Apparent Viscosity $V_{600}$ (cps) | Plastic Viscosity (cps) | Yield Value (lb/1000 ft$^2$) | Thixotropy $V_{300}/V_{600}$ |
| --- | --- | --- | --- | --- | --- | --- | --- |
| Purified bentonite (non-treated) | | 2 | 3.5 | 3.0 | 2.5 | 1.0 | 1.17 |
| | | 3 | 6.5 | 5.5 | 4.5 | 2.0 | 1.18 |
| | | 5 | 33.0 | 23.8 | 14.5 | 18.5 | 1.39 |
| Commercially available purified bentonite ("Kunipia G" produced by Kunimine Kogyo K.K.) | | 1 | 3.0 | 2.5 | 2.0 | 1.0 | 1.20 |
| | | 2 | 6.0 | 5.3 | 4.5 | 1.5 | 1.13 |
| | | 3 | 16.0 | 13.8 | 11.5 | 4.5 | 1.16 |
| Sample 1 | methyltrimethoxysilane | 2 | 9.0 | 7.0 | 5.0 | 4.0 | 1.29 |
| | | 3 | 33.5 | 22.5 | 11.5 | 22.0 | 1.49 |
| | | 5 | 74.0 | 55.3 | 36.5 | 37.5 | 1.34 |
| Sample 2 | methyltriethoxysilane | 2 | 8.5 | 6.8 | 5.0 | 3.5 | 1.25 |
| | | 3 | 17.0 | 12.8 | 8.5 | 8.5 | 1.33 |
| | | 5 | 70.0 | 55.0 | 40.0 | 30.0 | 1.27 |
| Sample 3 | propyltrimethoxysilane | 2 | 8.5 | 6.3 | 4.0 | 4.5 | 1.35 |
| | | 3 | 24.5 | 16.0 | 7.5 | 17.0 | 1.53 |
| Sample 4 | butyltrimethoxysilane | 2 | 14.0 | 9.5 | 5.0 | 9.0 | 1.47 |
| | | 3 | 42.0 | 24.0 | 6.0 | 36.0 | 1.75 |
| Sample 5 | hexyltrimethoxysilane | 1 | 6.5 | 4.8 | 3.0 | 3.5 | 1.35 |
| | | 2 | 38.5 | 22.0 | 5.5 | 33.0 | 1.75 |
| | | 3 | 105.0 | 57.8 | 10.5 | 94.5 | 1.82 |
| Sample 6 | octyltriethoxysilane | 1 | 5.0 | 3.8 | 2.5 | 2.5 | 1.32 |
| | | 2 | 31.5 | 19.0 | 6.5 | 25.0 | 1.66 |
| | | 3 | 83.5 | 46.8 | 10.0 | 73.5 | 1.78 |
| Sample 7 | dodecyltriethoxysilane | 1 | 7.0 | 5.0 | 3.0 | 4.0 | 1.40 |
| | | 2 | 40.0 | 23.3 | 6.5 | 33.5 | 1.72 |
| | | 3 | 123.0 | 67.5 | 12.0 | 111.0 | 1.82 |
| Sample 8 | octadecyltriethoxysilane | 1 | 6.5 | 5.0 | 3.5 | 3.0 | 1.30 |
| | | 2 | 29.5 | 18.0 | 6.5 | 23.0 | 1.64 |
| | | 3 | 82.5 | 44.5 | 6.5 | 76.0 | 1.85 |

Note:
*Part by weight per 100 parts by weight of water

As is apparent from the results of Table 1, the aqueous dispersion solutions of Samples 1 to 8 are markedly superior to the non-treated purified bentonite or the commercially available purified bentonite in apparent viscosity, yield value, and thixotropy, and further the alkyltrialkoxysilane-modified bentonite according to the present invention exhibits an excellent function in rheological adjustment of an aqueous liquid system.

EXAMPLE 2

In 20 kg of deionized water was poured 400 g of bentonite produced in Wyoming, U.S.A. and allowed to stand overnight to be swollen. The mixture was dispersed with a disper for 1 hour. The resulting bentonite suspension was allowed to stand for 3 days to sediment non-clay substances. The purified bentonite sol (16 kg; solids content: 1.39%) of the upper phase was obtained by decantation.

In a 5000 ml-volume stainless steel beaker was put 1,440 g of the purified bentonite sol (corresponding to 20 g of water-free bentonite) and heated to 60° C. while stirring with a disper. Separately, 7.0 g of dimethyloctadecylbenzylammonium chloride was dissolved in 70 ml of deionized water at 60° C., and 2.0 parts of octadecyltriethoxysilane or methyltrimethoxysilane per 100 parts of bentonite was further dissolved therein by stirring. The solution was added to the bentonite sol, and the mixture was stirred for 30 minutes, followed by filtration. The filter cake was washed with water, dehydrated, dried to a water content of 5%, and ground in Bantam Mill (manufactured by Hosokawa K.K.) (Samite products shown in Table 2 below in terms of swellability in toluene and rheological characteristics when dispersed in toluene. The swellability was measured by putting 100 ml of toluene in a measuring cylinder, adding 2.0 g of a test sample, and measuring the total volume after 24 hours at 20° C. The viscosity was measured by dispersing 3.0 g of a test sample in 150 g of toluene in a homogenizer at 10,000 rpm for 2 minutes and immediately measuring the apparent viscosity at 6 rpm or 60 rpm ($V_6$ or $V_{60}$) at 20° C. with a BL type viscometer. The thixotropy was expressed in terms of a $V_6/V_{60}$ ratio. The results obtained are shown in Table 2.

TABLE 2

| Sample | Silane Treating Agent (part*1) | Swellability (ml/2 g) | Apparent Viscosity $V_6$ (cps) | Apparent Viscosity $V_{60}$ (cps) | Thixotropy ($V_6/V_{60}$) |
| --- | --- | --- | --- | --- | --- |
| Sample 201 | octadecyltriethoxysilane (2.0) | 47 | 580 | 96 | 6.40 |
| Sample 202 | methyltrimethoxysilane (2.0) | 48 | 850 | 168 | 5.06 |
| BENTONE SD-1*2 | — | 38 | 120 | 22 | 5.45 |
| BENTONE SD-2*2 | — | 45 | 188 | 21 | 8.95 |
| BENTONE SD-3*2 | — | 27 | 108 | 19 | 5.68 |
| BENTONE 27*2 | — | 20 | 70 | 17 | 4.12 |
| BENTONE 34*2 | — | 40 | 150 | 36 | 4.17 |

TABLE 2-continued

| Sample | Silane Treating Agent (part[1]) | Swellability (ml/2 g) | Apparent Viscosity | | Thixotropy ($V_6/V_{60}$) |
|---|---|---|---|---|---|
| | | | $V_6$ (cps) | $V_{60}$ (cps) | |
| BENTONE 38[2] | — | 31 | 150 | 33 | 4.55 |
| BENTONE 500[2] | — | 32 | 200 | 36 | 5.56 |
| NEW D ORBEN[3] | — | 32 | 120 | 22 | 5.45 |
| TIXOGEL VZ[4] | — | 37 | 155 | 36 | 4.31 |
| S BEN[5] | — | 22 | 80 | 23 | 3.48 |
| ORGANITE T[5] | — | 29 | 95 | 28 | 3.39 |
| ORGANITE[5] | — | 32 | 205 | 52 | 3.94 |

Note:
[1] Part by weight per 100 parts by weight of bentonite (i.e. water-free bentonite).
[2] Trade name of the product of Rheox Inc., U.S.A.
[3] Trade name of the product of Shiraishi Kogyo K.K.
[4] Trade name of the product of Süd-Chemie AG, German.
[5] Trade name of the product of Nihon Yuki Nendo K.K.

Note: *1: Part by weight per 100 parts by weight of bentonite (i.e. water-free bentonite).
*2: Trade name of the product of Rheox Inc., U.S.A.
*3: Trade name of the product of Shiraishi Kogyo K.K.
*4: Trade name of the product of Sud-Chemie AG, German.
*5: Trade name of the product of Nihon Yuki Nendo K.K.

As is apparent from the results of Table 2, the alkyltrialkoxysilane-modified bentonite according to the present invention has a higher swellability, a higher apparent viscosity, and sufficient thixotropic properties in toluene alone as compared with any of the commercially (conventionally) available organophilic modified bentonite products and therefore performs excellent functions in adjustment of rheology of a hydrocarbon solvent system.

As described and demonstrated above, the present invention provides modified bentonite which is obtained by treating bentonite with an alkyltrialkoxysilane to make a part of the surface thereof hydrophobic without causing water repellency and which, when dispersed in an aqueous liquid, considerably increases the apparent viscosity of the aqueous liquid to perform excellent rheology adjusting functions.

The present invention further provides organophilic modified bentonite which is obtained by treating bentonite with a quaternary ammonium cation and an alkyltrialkoxysilane and which exhibits excellent dispersibility in a hydrocarbon solvent system, such as toluene, to perform excellent functions in adjusting rheology of such a system.

The modified bentonite according to the present invention satisfies the demand of rheological adjustment essential to various industrial liquid products, either aqueous or organic, such as coatings, printing inks, ceramic slurries, sealants, and cosmetics.

While the invention has been described in detail and with reference to specific examples thereof, it will be apparent to one skilled in the art that various changes and modifications can be made therein without departing from the spirit and scope thereof.

What is claimed is:

1. Modified bentonite which can be dispersed in water to perform a function of adjusting rheology of an aqueous liquid, which is obtained by
    adding at least one alkyltrialkoxysilane represented by formula (I):

$$R^1Si(OR^2)_3 \qquad (I)$$

wherein $R^1$ represents a saturated alkyl group having from 1 to 22 carbon atoms; and R represents a methyl group, an ethyl group, a propyl group or a butyl group, to bentonite in such an amount that the resulting product can retain an excellent water-dispersibility, and then
    stirring and pulverizing the mixture in a water-free atmosphere to add an alkylsilyl group to a part of the surface of bentonite particles.

2. Modified bentonite as claimed in claim 1, wherein said bentonite is purified water-free bentonite prepared by removing non-clay substances from a bentonite aqueous suspension using spontaneous sedimentation or centrifugal separation and drying the resulting purified bentonite sol.

3. Modified bentonite as claimed in claim 1, wherein said alkyltrialkoxysilane is used in an amount of from 0.5 to 15 parts by weight per 100 parts by weight of bentonite.

* * * * *

UNITED STATES PATENT AND TRADEMARK OFFICE
CERTIFICATE OF CORRECTION

PATENT NO. : 5,292,908

DATED : March 8, 1994

INVENTOR(S) : Masanobu Onikata, et al.

It is certified that error appears in the above-identified patent and that said Letters Patent is hereby corrected as shown below:

Column 7, lines 22-30 Delete entirely.
Column 8, line 29, change "R" to --$R^2$--.

Signed and Sealed this

Twenty-third Day of August, 1994

Attest:

BRUCE LEHMAN

Attesting Officer

Commissioner of Patents and Trademarks